(12) United States Patent
Niizaka

(10) Patent No.: US 11,821,851 B2
(45) Date of Patent: Nov. 21, 2023

(54) X-RAY IMAGING APPARATUS

(71) Applicant: Shimadzu Corporation, Kyoto (JP)

(72) Inventor: Takuma Niizaka, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 401 days.

(21) Appl. No.: 17/414,069

(22) PCT Filed: Dec. 20, 2018

(86) PCT No.: PCT/JP2018/046996
§ 371 (c)(1),
(2) Date: Jun. 15, 2021

(87) PCT Pub. No.: WO2020/129213
PCT Pub. Date: Jun. 25, 2020

(65) Prior Publication Data
US 2022/0057340 A1  Feb. 24, 2022

(51) Int. Cl.
*G01N 23/046* (2018.01)
*G06T 3/40* (2006.01)

(52) U.S. Cl.
CPC ......... *G01N 23/046* (2013.01); *G06T 3/4069* (2013.01); *G01N 2223/401* (2013.01)

(58) Field of Classification Search
CPC .......... G01N 23/046; G01N 2223/401; G01N 2223/42; G01N 2223/427; G01N 2223/66; G06T 3/4069; A61B 6/00
See application file for complete search history.

(56) References Cited

U.S. PATENT DOCUMENTS

| | | | |
|---|---|---|---|
| 7,492,967 B2 * | 2/2009 | Toki | G06T 3/4053 600/443 |
| 8,559,590 B2 * | 10/2013 | Partain | A61B 6/032 378/21 |

(Continued)

FOREIGN PATENT DOCUMENTS

| | | | | |
|---|---|---|---|---|
| JP | 4519434 B2 | 8/2010 | | |
| JP | 2012196451 A | * | 10/2012 | .............. A61B 6/03 |
| JP | 2016-517961 A | 6/2016 | | |

OTHER PUBLICATIONS

International Search Report (with English translation) and Written Opinion (with Machine translation) dated Mar. 12, 2019 in corresponding International Application No. PCT/JP2018/046996; 9 pages.

(Continued)

*Primary Examiner* — Kiho Kim
(74) *Attorney, Agent, or Firm* — Maier & Maier, PLLC

(57) ABSTRACT

In an X-ray imaging apparatus, an image processor is configured to generate a super-resolved image having higher resolution in an X direction than a first fluoroscopic X-ray image and a second fluoroscopic X-ray image by dividing, in the X direction, a pixel value of a first pixel in the first fluoroscopic X-ray image based on pixel values of two pixels in the second fluoroscopic X-ray image that overlap the first pixel when the first fluoroscopic X-ray image and the second fluoroscopic X-ray image are shifted in the X direction by an amount corresponding to a movement amount (of an X-ray detection position) and displayed in an overlapping manner.

8 Claims, 8 Drawing Sheets

(56) References Cited

U.S. PATENT DOCUMENTS 9,459,217 B2 10/2016 Wang et al.
2016/0047759 A1\* 2/2016 Wang .................. G01N 23/046
378/11

OTHER PUBLICATIONS

Peter Cheeseman et al., "Super-Resolved Surface Reconstruction From Multiple Images", Technical Report FIA 94 12, Dec. 14, 1994, 15 pages.

\* cited by examiner

X-RAY IMAGING APPARATUS

FIELD

The present invention relates to an X-ray imaging apparatus, and more particularly, it relates to an X-ray imaging apparatus that generates a super-resolved image having higher resolution than first and second images generated based on X-rays detected at first and second positions.

BACKGROUND

Conventionally, an X-ray imaging apparatus that generates a super-resolved image having higher resolution than first and second images generated based on X-rays detected at first and second positions is known (see Patent Document 1, for example).

Patent Document 1 discloses an X-ray imaging apparatus including an X-ray generator that emits an X-ray beam, a radiation detector having a plane arranged perpendicular to the emission direction of the X-ray beam, a translation stage that holds the radiation detector and translates the radiation detector in a pixel direction. In the X-ray imaging apparatus disclosed in Patent Document 1, the radiation detector is moved to different detection positions by being translated by the translation stage by a distance finer than the pixel size. Then, based on a plurality of radiographs (images) acquired at the different detection positions, an image (super-resolved image) with finer resolution than the acquired radiographs is generated.

PRIOR ART

Patent Document

Patent Document 1: Japanese Translation of PCT Application No. 2016-517961

SUMMARY

Although not described in Patent Document 1, when a super-resolved image is generated based on a plurality of acquired images as in a conventional X-ray imaging apparatus as disclosed in Patent Document 1, it is known that sequential calculation using a large number of parameters is performed. When the sequential calculation is performed, the calculation time tends to be relatively long. When a large number of parameters are used, the image quality of the generated super-resolved image is easily affected by the parameters, and a certain super-resolution effect (an effect of increasing the resolution without degrading the image quality) may not be obtained. Therefore, in the conventional X-ray imaging apparatus as disclosed in Patent Document 1, the calculation time for generating a super-resolved image based on a plurality of acquired images disadvantageously becomes long, and a certain super-resolution effect may not be obtained in the generated super-resolved image.

The present invention is intended to solve at least one of the above problems. The present invention aims to provide an X-ray imaging apparatus capable of generating a super-resolved image while significantly reducing or preventing an increase in the calculation time when generating the super-resolved image and ensuring a certain super-resolution effect.

In order to attain the aforementioned object, an X-ray imaging apparatus according to an aspect of the present invention includes an X-ray source, a detector configured to detect X-rays radiated from the X-ray source at a first position and a second position translated in a first direction by a movement amount smaller than a pixel size of the detector from the first position, an image processor configured to generate a first image based on the X-rays detected at the first position, the image processor being configured to generate a second image based on the X-rays detected at the second position, and a moving mechanism configured to move an X-ray detection position of the detector between the first position and the second position. The image processor is configured to generate a super-resolved image having higher resolution in the first direction than the first image and the second image based on a divided image that has undergone a division process in the first direction to divide, in the first direction, a pixel value of a first pixel in one of the first image and the second image based on pixel values of two pixels in the other of the first image and the second image that overlap the first pixel when the first image and the second image are shifted in the first direction by an amount corresponding to the movement amount and displayed in an overlapping manner.

In the X-ray imaging apparatus according to this aspect of the present invention, as described above, the image processor is configured to generate the super-resolved image having higher resolution in the first direction than the first image and the second image based on the divided image that has undergone the division process in the first direction to divide, in the first direction, the pixel value of the first pixel in one of the first image and the second image based on the pixel values of the two pixels in the other of the first image and the second image that overlap the first pixel when the first image and the second image are shifted in the first direction by the amount corresponding to the movement amount and displayed in an overlapping manner. When the first image and the second image are shifted in the first direction by the amount corresponding to the movement amount and displayed in the overlapping manner, the two pixels in the other of the first image and the second image that overlap the first pixel are pixels partially shifted to the first side and the second side of the first pixel, respectively, in the first direction. That is, the two pixels in the other of the first image and the second image that overlap the first pixel can be considered as reference values for dividing the pixel value of the first pixel into the first side and the second side in the first direction. Accordingly, with the above configuration, the pixel value of the first pixel can be divided in the first direction in consideration of the distribution of the actual pixel values by relatively simple calculation of dividing the pixel value based on the pixel values of the two pixels. That is, the calculation of simply dividing the pixel value based on the pixel values of the two pixels is used, and thus it is not necessary to use sequential calculation performed in the conventional super-resolution process and a large number of parameters. Furthermore, the pixel is divided in consideration of the distribution of the actual pixel values, and thus the super-resolved image having higher resolution at least in the first direction than the first image and the second image, in which a certain level of image quality is ensured, can be generated. Consequently, the super-resolved image can be generated while an increase in the calculation time for generating the super-resolved image is significantly reduced or prevented and a certain super-resolution effect (the effect of increasing the resolution without degrading the image quality) is ensured.

In the aforementioned X-ray imaging apparatus according to this aspect, the image processor is preferably configured to generate the super-resolved image based on the divided image obtained by performing the division process on the pixel value of the first pixel in one of the first image and the second image based on the pixel values of the two pixels in the other of the first image and the second image that overlap the first pixel and an overlapping area ratio when the first image and the second image are shifted in the first direction by the amount corresponding to the movement amount and displayed in the overlapping manner. Accordingly, in addition to the pixel values of the two pixels that overlap the first pixel, the overlapping area ratio of the two pixels is taken into consideration, and thus the first pixel can be divided in the first direction while the distribution of the actual pixel values is more accurately considered. Consequently, as compared with a case in which the overlapping area ratio of the two pixels is not taken into consideration, the super-resolved image having higher resolution at least in the first direction than the first image and the second image and a better image quality can be generated.

In the aforementioned X-ray imaging apparatus according to this aspect, the image processor is preferably configured to generate the super-resolved image based on a first divided image obtained by performing the division process on the pixel value of the first pixel in the first image based on the pixel values of the two pixels in the second image that overlap the first pixel when the first image and the second image are shifted in the first direction by the amount corresponding to the movement amount and displayed in the overlapping manner, and a second divided image obtained by performing the division process on a pixel value of a second pixel in the second image based on pixel values of two pixels in the first image that overlap the second pixel when the first image and the second image are shifted in the first direction by the amount corresponding to the movement amount and displayed in the overlapping manner. Accordingly, the super-resolved image is generated in consideration of both the first divided image and the second divided image, and thus the accuracy of dividing the pixel value in the first direction can be improved as compared with a case in which the super-resolved image is generated in consideration of only one of the first divided image and the second divided image. Consequently, as compared with a case in which the super-resolved image is generated in consideration of only one of the first divided image and the second divided image, the super-resolved image having higher resolution at least in the first direction than the first image and the second image and a better image quality can be generated.

In this case, the image processor is preferably configured to generate the super-resolved image by generating an average image obtained by averaging a pixel of the first divided image and a pixel of the second divided image corresponding to each other. Accordingly, an error that occurs between the first divided image and the second divided image can be reduced as compared with a case in which the average image is not generated, and thus the accuracy of dividing the pixel value in the first direction can be easily improved.

In the aforementioned X-ray imaging apparatus according to this aspect, the detector is preferably configured to detect X-rays at a third position and a fourth position respectively translated in a second direction orthogonal to the first direction by the movement amount smaller than the pixel size of the detector from the first position and the second position, in addition to the first position and the second position, and the image processor is preferably configured to generate the first image, the second image, a third image, and a fourth image based on the X-rays detected at the first position, the second position, the third position, and the fourth position, respectively, and to generate the super-resolved image having higher resolution in the first and second directions than the first image, the second image, the third image, and the fourth image by performing, in the second direction, a same process as the division process in the first direction based on the divided image that has undergone the division process in the first direction based on the first image and the second image, and the divided image that has undergone the division process in the first direction based on the third image and the fourth image. Accordingly, the super-resolved image having high resolution in the second direction in addition to the first direction, in which a certain level of image quality is ensured, can be generated, and thus as compared with a case in which the resolution is high only in the first direction, the super-resolved image in which the degree of resolution is not biased in the first direction and the second direction can be generated. Furthermore, pixels in a general display device have the same size in the row direction and the column direction of detection elements arranged in a matrix, and thus a post-process to display the super-resolved image on a display device such as an image interpolation process to adjust the pixel sizes in the first and second directions can be simplified unlike a case in which the resolution is different in the first and second directions.

In the aforementioned X-ray imaging apparatus according to this aspect, the image processor is preferably configured to virtually generate, based on a pixel value of one overlapping pixel, another overlapping pixel when there is only one pixel that overlaps the first pixel of one of the first image and the second image at an end of the other of the first image and the second image when the first image and the second image are shifted in the first direction by the amount corresponding to the movement amount and displayed in the overlapping manner. Accordingly, another overlapping pixel is virtually generated such that even when there is only one pixel that overlaps the first pixel located at the end, calculation of dividing the first pixel in the first direction can be reliably performed.

In the aforementioned configuration including the image processor configured to generate the super-resolved image based on the divided image obtained by performing the division process on the pixel value of the first pixel based on the pixel values of the two pixels that overlap the first pixel and the overlapping area ratio, the detector is preferably configured to detect the X-rays radiated from the X-ray source at the first position and the second position translated in the first direction by a distance equal to a length half the pixel size of the detector from the first position. Accordingly, the overlapping area ratio of the two pixels is equal (1:1), and thus the pixel value of the first pixel can be divided in the first direction using the ratio of the pixel values themselves of the two pixels that overlap the first pixel. Consequently, calculation in the division process can be simplified as compared with a case in which division is performed using the overlapping area ratio of the two pixels other than ½, and thus an increase in the calculation time for generating the super-resolved image can be further significantly reduced or prevented.

In the aforementioned X-ray imaging apparatus according to this aspect, the detector is preferably configured to perform tomographic imaging by alternately repeating detection operation to detect the X-rays radiated from the X-ray source from a plurality of directions while rotating with a third direction as a rotation axis and translation in the third direction. Accordingly, in the X-ray imaging apparatus that performs (so-called non-helical scan-type) tomographic imaging as described above, the super-resolved image can be generated while an increase in the calculation time for generating the super-resolved image is significantly reduced or prevented and a certain super-resolution effect is ensured.

Effect of the Invention

According to the present invention, as described above, it is possible to generate the super-resolved image while significantly reducing or preventing an increase in the calculation time when generating the super-resolved image and ensuring a certain super-resolution effect.

DETAILED DESCRIPTION

An embodiment embodying the present invention is hereinafter described on the basis of the drawings.

The configuration of an X-ray imaging apparatus 100 according to the embodiment of the present invention is now described with reference to FIGS. 1 to 9.

Figure 1:
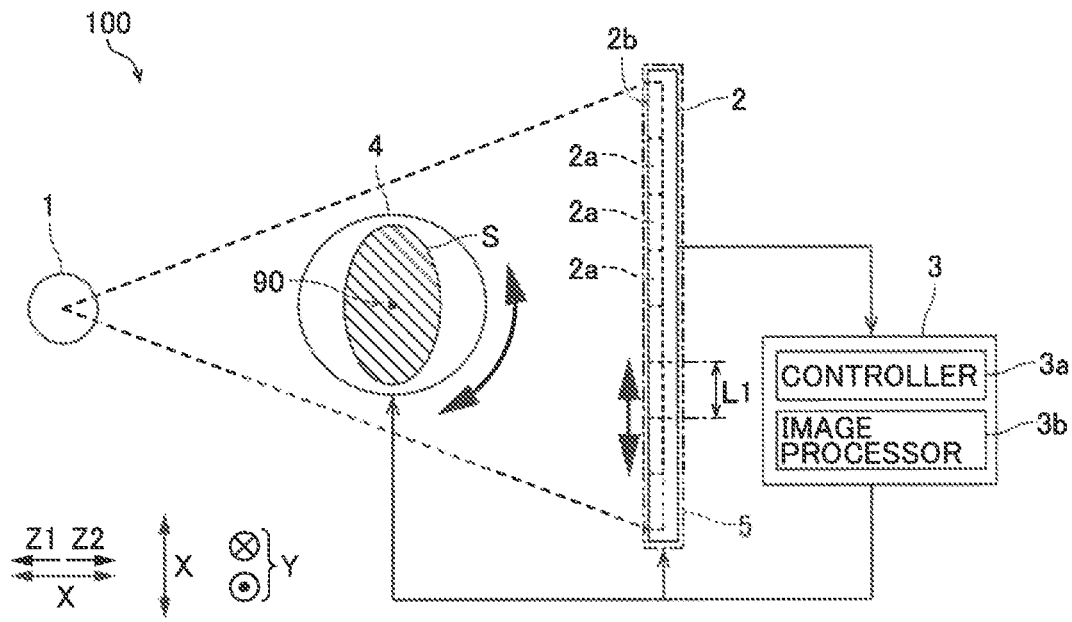
FIG. 1 is a diagram showing the overall configuration of an X-ray imaging apparatus according to an embodiment of the present invention as viewed in a Y direction.

As shown in FIG. 1, the X-ray imaging apparatus 100 includes an X-ray source 1, a detector 2, a processing unit 3, a rotating stage 4, and a detector moving mechanism 5. The detector moving mechanism 5 is an example of a "moving mechanism" in the claims.

In the X-ray imaging apparatus 100, the X-ray source 1, the rotating stage 4, and the detector 2 are arranged side by side in this order in a direction (Z direction) connecting the X-ray source 1 to the detector 2. In this description, a direction from the X-ray source 1 toward the detector 2 is defined as a Z2 direction, and the opposite direction is defined as a Z1 direction. A direction in which the rotating stage 4 translates in an in-plane direction orthogonal to the Z direction is defined as a Y direction. A direction orthogonal to the Z direction and the Y direction is defined as an X direction. The X direction is an example of a "first direction" or a "row direction" in the claims. The Y direction is an example of a "second direction" or a "column direction" in the claims.

The X-ray source 1 is an X-ray generator capable of generating X-rays by a high voltage applied thereto. The X-ray source 1 radiates the generated X-rays in the Z2 direction.

The detector 2 detects the X-rays radiated from the X-ray source 1 and converts the detected X-rays into electric signals. The detector 2 has a detection surface 2b including a plurality of detection elements 2a arranged side by side in a matrix in the X direction and the Y direction at a predetermined period L1. The detector 2 includes a plurality of conversion elements (not shown) that are arranged so as to correspond to the plurality of detection elements 2a, respectively, and change the detected X-rays into electric signals. The detector 2 is a flat panel detector (FPD), for example. The detection signals (electric signals) converted by the detector 2 are transmitted to an image processor 3b (described below) of the processing unit 3.

The processing unit 3 includes a controller 3a and the image processor 3b.

The controller 3a controls the operation of the rotating stage 4 and the detector moving mechanism 5. The controller 3a includes a central processing unit (CPU), a read-only memory (ROM), and a random access memory (RAM), for example.

The image processor 3b generates a fluoroscopic X-ray image Ia (see FIG. 4) based on the detection signals transmitted from the detector 2. Furthermore, the image processor 3b generates a reconstructed image 70x (see FIG. 8) described below based on a plurality of fluoroscopic X-ray images Ia (see FIG. 4). The image processor 3b includes a processor such as a graphics processing unit (GPU) or a field-programmable gate array (FPGA) configured for image processing, for example. Data of each pixel Ea (E) in the fluoroscopic X-ray image Ia (see FIG. 4) corresponds to an X-ray dose detected by each detection element 2a of the detector 2.

Figure 2:
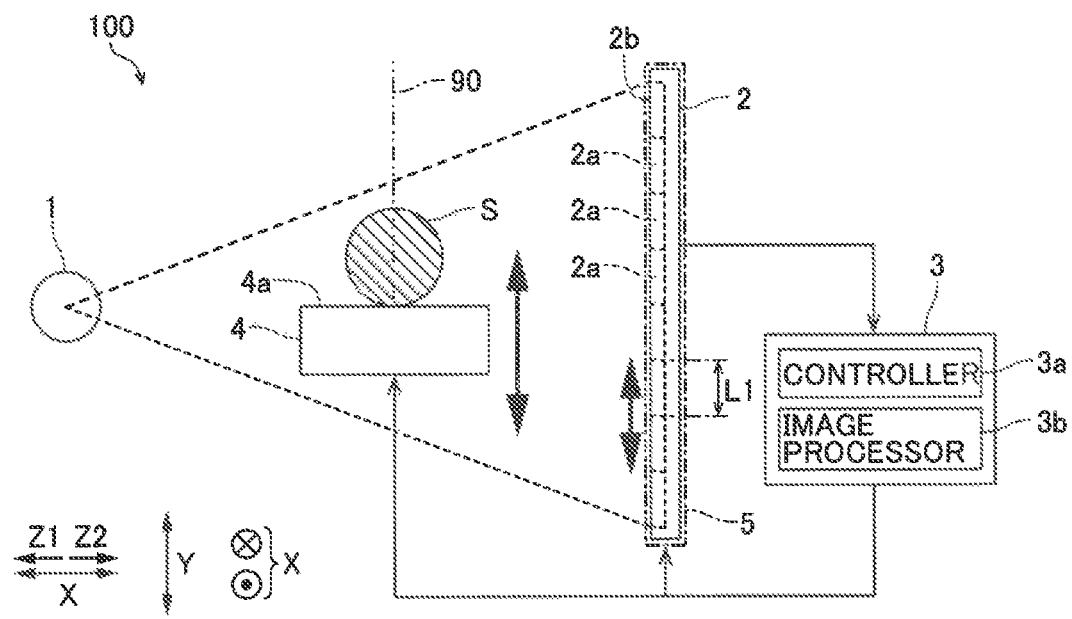
FIG. 2 is a diagram showing the overall configuration of the X-ray imaging apparatus according to the embodiment of the present invention as viewed in an X direction.

The rotating stage 4 has a placement surface 4a (see FIG. 2) on which a subject S is placed. The rotating stage 4 can rotate 360 degrees about a rotation axis 90 along the Y direction in an XZ plane. As shown in FIG. 2, the rotating stage 4 can translate in the Y direction. Thus, in this embodiment, the detector 2 can perform tomographic imaging by alternately repeating detection operation to detect X-rays radiated from the X-ray source 1 from a plurality of directions (in the XZ plane) while rotating with the Y direction as a rotation axis and translation in the Y direction. That is, the X-ray imaging apparatus 100 is an imaging apparatus capable of performing so-called non-helical scan-type tomographic imaging.

Figure 3:
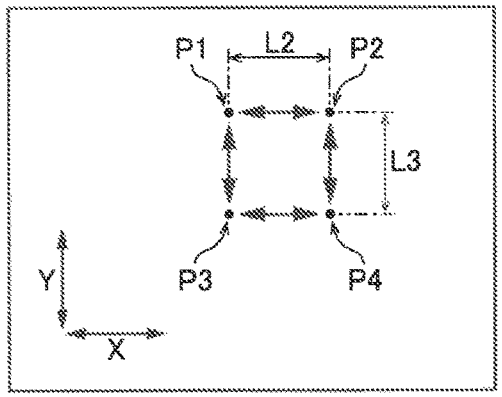
FIG. 3 is a diagram illustrating detection positions of X-rays in the X-ray imaging apparatus according to the embodiment of the present invention.

As shown in FIGS. 1 and 2, the detector moving mechanism can move the detector 2 in the X direction and the Y direction by a movement amount smaller than the detection element 2a. Thus, as shown in FIG. 3, the detector moving mechanism 5 can move the detector 2 between a first position P1, a second position P2, a third position P3, and a fourth position P4. The second position P2 is a position translated from the first position P1 by a distance L2 in the X direction. The third position P3 is a position translated from the first position P1 by a distance L3 in the Y direction. The fourth position is a position translated to the same side as the third position translated from the first position P1 by the distance L3 in the Y direction. The distance L2 and the distance L3 are distances smaller than the size (the period in which the detection elements 2a are aligned) L1 of one detection element 2a in the X direction and the Y direction, respectively. In the X-ray imaging apparatus 100, each of the distance L2 and the distance L3 is a distance (length) equal to half the size L1 of one detection element 2a in the X direction and the Y direction. That is, in this embodiment, the detector 2 can detect X-rays radiated from the X-ray source 1 at the first position P1, the second position P2, which is translated in the X direction by a distance equal to a length L5 (see FIG. 5) of half of one pixel Ea (having a length L4 (see FIG. 5)) from the first position P1, and the third position P3 and the fourth position P4, which are translated in the Y direction by the distance equal to the length L5 (see FIG. 5) of half of one pixel Ea (having the length L4 (see FIG. 5)) from the first position P1 and the second position P2, respectively.

Figure 4:
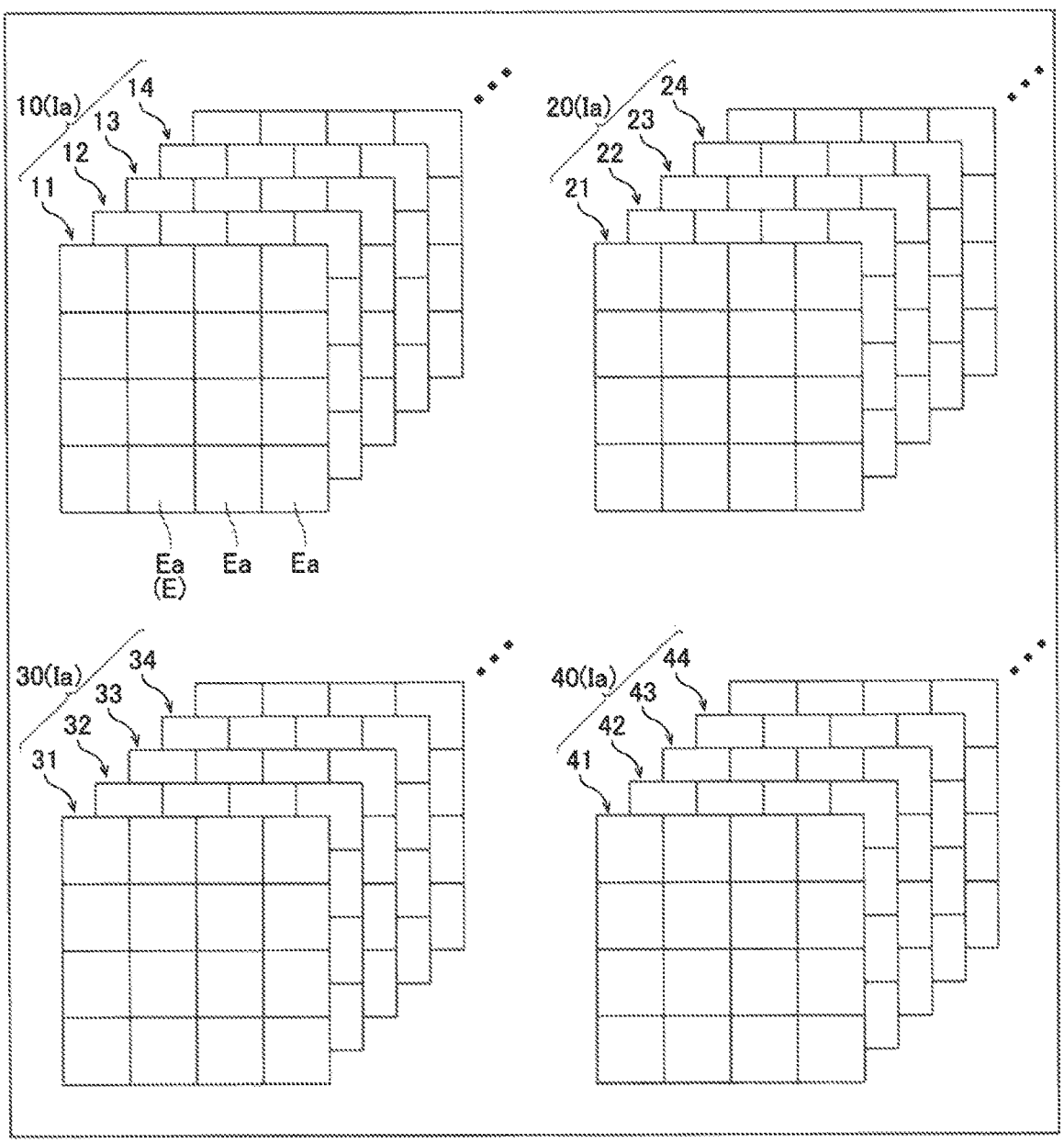
FIG. 4 is a diagram illustrating fluoroscopic X-ray images captured by the X-ray imaging apparatus according to the embodiment of the present invention.

With the above configuration, as shown in FIG. 4, the image processor 3b can generate, as fluoroscopic X-ray images Ia, a first fluoroscopic X-ray image 10, a second fluoroscopic X-ray image 20, a third fluoroscopic X-ray image 30, and a fourth fluoroscopic X-ray image 40 based on the X-rays detected at the first position P1, the second position P2, the third position P3, and the fourth position P4, respectively. The first fluoroscopic X-ray image 10, the second fluoroscopic X-ray image 20, the third fluoroscopic X-ray image 30, and the fourth fluoroscopic X-ray image 40 are examples of a "first image", a "second image", a "third image", and a "fourth image" in the claims, respectively.

The first fluoroscopic X-ray image 10, the second fluoroscopic X-ray image 20, the third fluoroscopic X-ray image 30, and the fourth fluoroscopic X-ray image 40 each include a plurality of fluoroscopic X-ray images Ia acquired by tomographic imaging using the rotating stage 4. That is, the first fluoroscopic X-ray image 10 includes first fluoroscopic X-ray images 11, 12, 13, 14, . . . , in which at least one of the imaging directions in the XZ plane or the imaging positions in the Y direction are different from each other due to the rotating stage 4. The second fluoroscopic X-ray image 20 includes second fluoroscopic X-ray images 21, 22, 23, 24, . . . , in which at least one of the imaging directions in the XZ plane or the imaging positions in the Y direction are different from each other due to the operation of the rotating stage 4. The third fluoroscopic X-ray image 30 includes third fluoroscopic X-ray images 31, 32, 33, 34, . . . , in which at least one of the imaging directions in the XZ plane or the imaging positions in the Y direction are different from each other due to the operation of the rotating stage 4. The fourth fluoroscopic X-ray image 40 includes fourth fluoroscopic X-ray images 41, 42, 43, 44, . . . , in which at least one of the imaging directions in the XZ plane or the imaging positions in the Y direction are different from each other due to the operation of the rotating stage 4.

Figure 5:
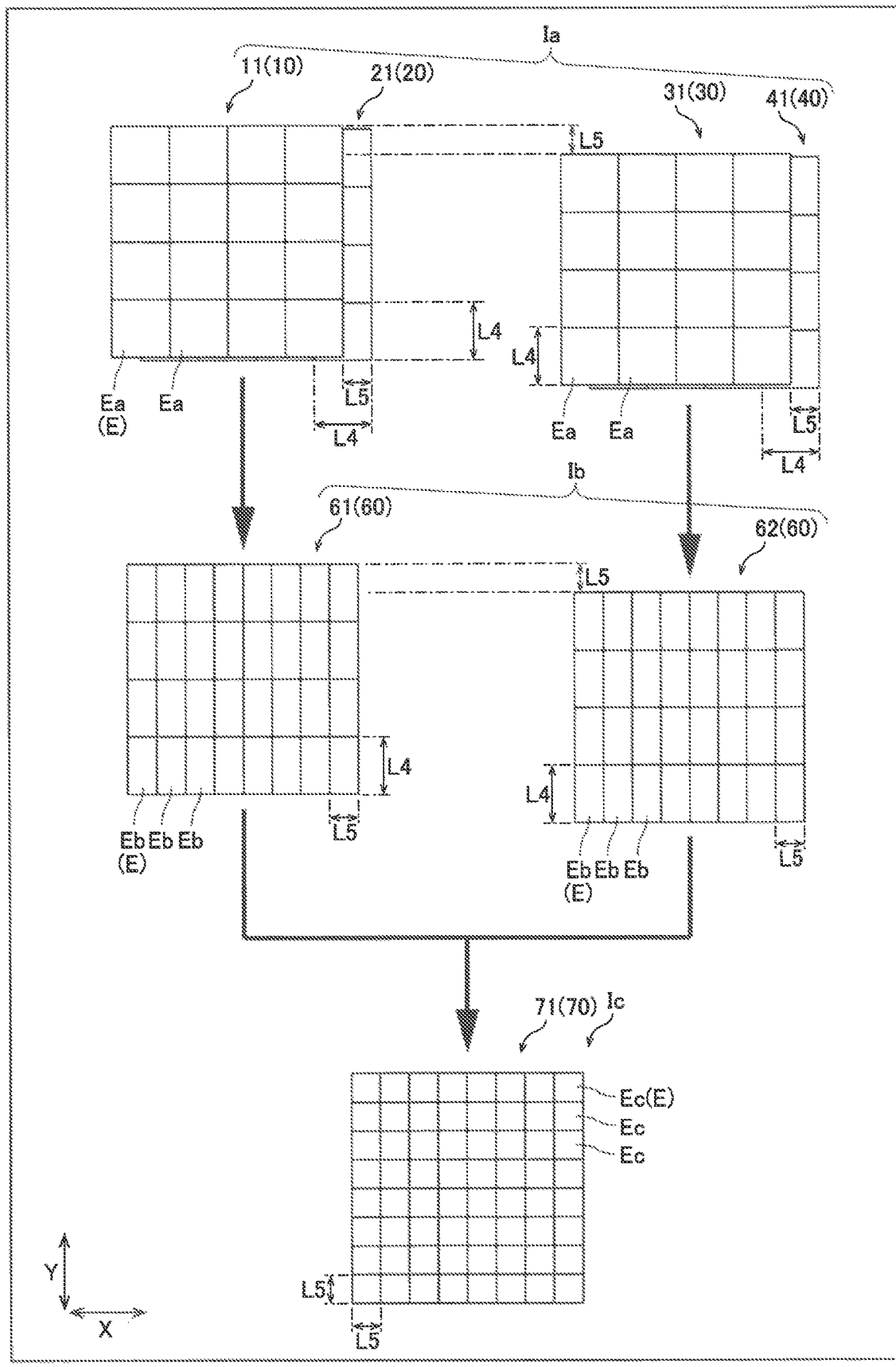
FIG. 5 is a diagram illustrating a super-resolution process in the X-ray imaging apparatus according to the embodiment of the present invention.

As shown in FIG. 5, the first fluoroscopic X-ray image 10 and the second fluoroscopic X-ray image 20 are data in which the imaging positions are different by L5, which is half the size L4 of one pixel Ea, in the X direction. The third fluoroscopic X-ray image 30 and the fourth fluoroscopic X-ray image 40 are data in which the imaging positions are different by L5, which is half the size L4 of one pixel Ea, in the X direction. The first and second fluoroscopic X-ray images 10 and 20 and the third and fourth fluoroscopic X-ray images 30 and 40 are data in which the imaging positions are different by L5, which is half the size L4 of one pixel Ea, in the Y direction. FIG. 5 shows a state in which the first fluoroscopic X-ray image 10 and the second fluoroscopic X-ray image 20 are shifted in the X direction by an amount corresponding to a movement amount (of the X-ray detection position) and displayed in an overlapping manner, and the third fluoroscopic X-ray image 30 and the fourth fluoroscopic X-ray image 40 are shifted in the X direction by an amount corresponding to a movement amount (of the X-ray detection position) and displayed in an overlapping manner.

In this embodiment, the image processor 3b generates a super-resolved image Ib having higher resolution in the X direction than the first fluoroscopic X-ray image 10 and the second fluoroscopic X-ray image 20 based on the first fluoroscopic X-ray image 10 (fluoroscopic X-ray image Ia) and the second fluoroscopic X-ray image 20 (fluoroscopic X-ray image Ia). In the following description, a process to generate an image having resolution higher than that of an original image based on a plurality of images (original image) may be referred to as a "super-resolution process".

Figure 6A:
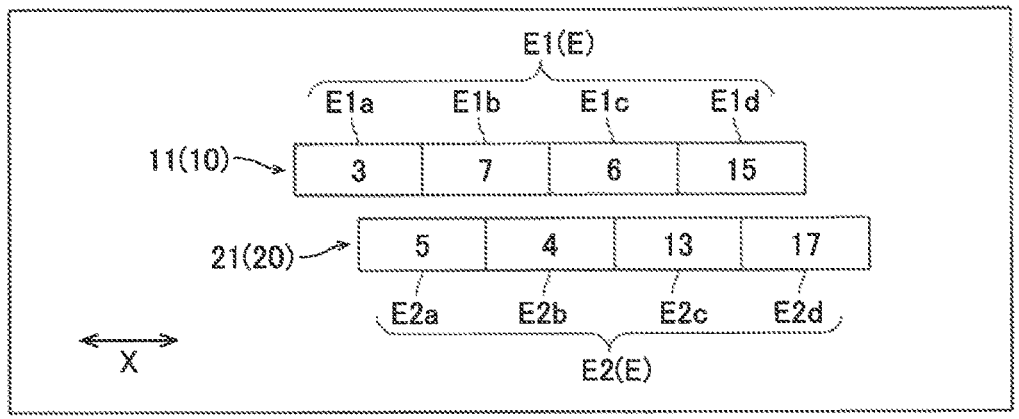
FIG. 6A is a diagram showing a portion of a first fluoroscopic X-ray image and a portion of a second fluoroscopic X-ray image that undergo the super-resolution process in the X direction.
Figure 6B:
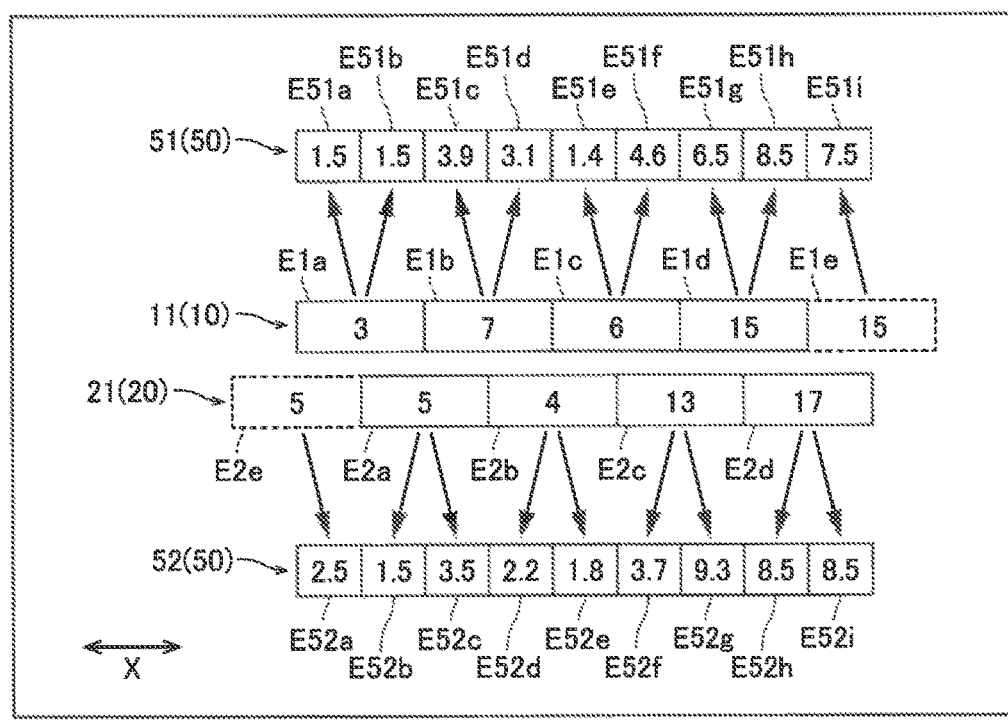
FIG. 6B is a diagram illustrating first and second divided images generated based on the first X-ray fluoroscopic image and the second X-ray fluoroscopic image.
Figure 6C:
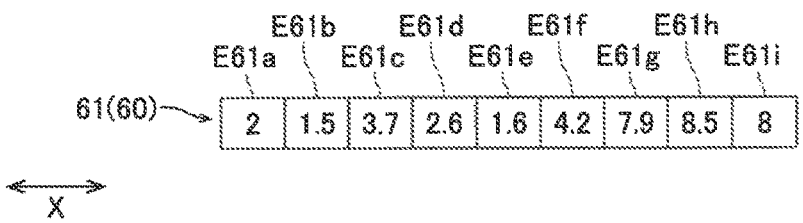
FIG. 6C is a diagram illustrating an average image obtained by averaging the first divided image and the second divided image.

Specifically, as shown in FIG. 6, the image processor 3b generates a super-resolved image Ib (see FIG. 5) having higher resolution in the X direction than the first fluoroscopic X-ray image 10 and the second fluoroscopic X-ray image 20 based on a divided image 51 (see FIG. 6B) that has undergone a division process in the X direction to divide the pixel values of pixels E1 (see FIG. 6A) in the first fluoroscopic X-ray image 10 in the X direction and a divided image 52 (see FIG. 6B) that has undergone a division process in the X direction to divide the pixel values of pixels E2 (see FIG. 6A) in the second fluoroscopic X-ray image 20 in the X direction. Furthermore, the image processor 3b generates a super-resolved image Ib (see FIG. 5) by generating an average image 60 (see FIG. 6C) obtained by averaging the divided image 51 (see FIG. 6B) and the divided image 52 (see FIG. 6B) in pixels E corresponding to each other. The pixels E1 and the pixels E2 are examples of a "first pixel" and a "second pixel" in the claims, respectively. The divided image 51 and the divided image 52 are examples of a "first divided image" and a "second divided image" in the claims, respectively.

The divided image 51 (see FIG. 6B) is a divided image 50 (see FIG. 6B) obtained by performing the division process in the X direction on the pixel value of each pixel E1 (see FIG. 6A) in the first fluoroscopic X-ray image 10 based on the pixel values of two pixels E2 in the second fluoroscopic X-ray image 20 that overlap the pixel E1 (see FIG. 6A) and the overlapping area ratio when the first fluoroscopic X-ray image 10 and the second fluoroscopic X-ray image 20 are shifted in the X direction by the amount corresponding to the movement amount (of the X-ray detection position) and displayed in an overlapping manner (as shown in FIG. 5). The divided image 52 (see FIG. 6B) is a divided image 50 (see FIG. 6B) obtained by performing the division process in the X direction on the pixel value of each pixel E2 (see FIG. 6A) in the second fluoroscopic X-ray image 20 based on the pixel values of two pixels E1 in the first fluoroscopic X-ray image 10 that overlap the pixel E2 (see FIG. 6A) and the overlapping area ratio. In FIG. 6, for convenience of illustration, only one row in the fluoroscopic X-ray image Ia is taken out and described. In FIGS. 6A and 6B, similarly to FIG. 5, the first fluoroscopic X-ray image 10 and the second fluoroscopic X-ray image 20 are shifted in the X direction by the amount corresponding to the movement amount (of the X-ray detection position) and displayed, and unlike FIG. 5 (displayed in an overlapping manner), for convenience of illustration, the first fluoroscopic X-ray image 10 and the second fluoroscopic X-ray image 20 are shifted in the upward-downward direction of the paper surface and displayed.

Specifically, as shown in FIG. 6B, the image processor 3b divides a pixel E1b in the first fluoroscopic X-ray image 10 into a pixel E51c and a pixel E51d that are pixels of the divided image 51. The image processor 3b sets the pixel values of the pixel E51c and the pixel E51d to values obtained by dividing the pixel value of the pixel E1b using a ratio of the pixel value of a pixel E2a and the pixel value of a pixel E2b in the second fluoroscopic X-ray image 20 that overlap the pixel E1b, respectively. For example, the image processor 3b sets a value (7×(5/(5+4))=3.9) and a value (7×(4/(5+4))=3.1) obtained by dividing the pixel value (7) of the pixel E1b using the ratio of the pixel value (5) of the pixel E2a and the pixel value (4) of the pixel E2b. That is, in the X-ray imaging apparatus 100, the image processor 3b divides the pixel value of each pixel E1 of the first fluoroscopic X-ray image 10 in half based on the pixel values of the two pixels E2 in the second fluoroscopic X-ray image 20 that overlap the pixel E1 in half.

The image processor 3b performs the same process on the other pixels E1 in the first fluoroscopic X-ray image 10. That is, the image processor 3b divides a pixel E1c in the first fluoroscopic X-ray image 10 into a pixel E51e and a pixel E51f that are the pixels E of the divided image 51. The image processor 3b sets the pixel values of the pixel E51e and the pixel E51f to values obtained by dividing the pixel value of the pixel E1c using a ratio of the pixel value of the pixel E2b and the pixel value of a pixel E2c in the second fluoroscopic X-ray image 20 that overlap the pixel E1c, respectively. Furthermore, the image processor 3b divides a pixel E1d in the first fluoroscopic X-ray image 10 into a pixel E51g and a pixel E51h that are the pixels of the divided image 51. The image processor 3b sets the pixel values of the pixel E51g and the pixel E51h to values obtained by dividing the pixel value of the pixel E1d using a ratio of the pixel value of the pixel E2c and the pixel value of a pixel E2d in the second fluoroscopic X-ray image 20 that overlap the pixel E1d, respectively.

In this embodiment, the image processor 3b virtually generates, based on the pixel value of one overlapping image E2, another overlapping pixel E2 when there is only one pixel E that overlaps the pixel E1 of the first fluoroscopic X-ray image 10 at the end of the second fluoroscopic X-ray image 20 when the first fluoroscopic X-ray image 10 and the second fluoroscopic X-ray image 20 are shifted in the X direction by the amount corresponding to the movement amount (of the X-ray detection position) and displayed in an overlapping manner (as shown in FIG. 5). Specifically, the image processor 3b divides a pixel E1a in the first fluoroscopic X-ray image 10 into a pixel E51a and a pixel E51b that are the pixels E of the divided image 51. The image processor 3b generates a virtual pixel E2e adjacent to the pixel E2a (at the end of the second fluoroscopic X-ray image 20) in the second fluoroscopic X-ray image 20 that overlaps the pixel E1a. Then, the image processor 3b sets the pixel values of the pixel E51a and the pixel E51b to values obtained by dividing the pixel value of the pixel E1a using a ratio of the pixel value of the pixel E2a and the pixel value of the (virtual) pixel E2d, respectively. In the X-ray imaging apparatus 100, the image processor 3b generates the pixel value of the virtual pixel E such that the pixel value of the virtual pixel E is equal to the pixel value of the adjacent pixel E.

The image processor 3b generates a pixel E at the end of the divided image 51 such that the number of pixels of the divided image 51 is equal to the number of pixels of the divided image 52. Specifically, the image processor 3b generates a pixel E51i based on a (virtual) pixel E1e adjacent to the (end) pixel E1d in the first fluoroscopic X-ray image 10. With the above configuration, the divided image 51 obtained by dividing the pixels E1 of the first fluoroscopic X-ray image 10 in the X direction is generated.

The image processor 3b generates the divided image 52 obtained by dividing the pixels E2 of the second fluoroscopic X-ray image 20 in the X direction by the same method (as in the generation of the divided image 51). That is, the image processor 3b divides the pixel E2a in the second fluoroscopic X-ray image 20 into a pixel E52b and a pixel E52c that are the pixels E of the divided image 52. The image processor 3b divides the pixel E2b in the second fluoroscopic X-ray image 20 into a pixel E52d and a pixel E52e that are the pixels E of the divided image 52. The image processor 3b divides the pixel E2c in the second fluoroscopic X-ray image 20 into a pixel E52f and a pixel E52g that are the pixels of the divided image 52. The image processor 3b divides the pixel E2d in the second fluoroscopic X-ray image 20 into a pixel E52h and a pixel E52i that are the pixels E of the divided image 52. The image processor 3b generates a pixel E52a based on the (virtual) pixel E2e adjacent to the (end) pixel E2a in the second fluoroscopic X-ray image 20 such that the number of pixels of the divided image 51 is equal to the number of pixels of the divided image 52. With the above configuration, the divided image 52 obtained by dividing the pixels E2 of the second fluoroscopic X-ray image 20 in the X direction is generated.

As shown in FIGS. 6B and 6C, the image processor 3b generates an average image 61 (60) obtained by averaging the pixel values of the pixels E in the divided image 51 and the divided image 52 corresponding to each other. That is, the image processor 3b averages the pixel value (1.5) of the pixel E51a of the divided image 51 and the pixel value (2.5) of the pixel E52a of the divided image 52 to obtain the pixel value (2) of a pixel E61a of the average image 61. The image processor 3b performs the same process on the other pixels. That is, the image processor 3b averages the pixel values of the pixels E51b, E51c, E51d, E51e, E51g, E51h, and E51i of the divided image 51 and the pixel values of the pixels E52b, E52c, E52d, E52e, E52g, E52h, and E52i of the divided image 52 to obtain the pixel values of pixels E61b, E61c, E61d, E61e, E61g, E61h, and E61i of the average image 61, respectively.

As shown in FIG. 5, the average image 61 (60) has higher (doubled) resolution in the X direction than the first fluoroscopic X-ray image 10 and the second fluoroscopic X-ray image 20. Specifically, in the X direction, the length L5 of one pixel Eb of the average image 61 (60) is half the length L4 of one pixel Ea of each of the first fluoroscopic X-ray image 10 and the second fluoroscopic X-ray image 20. That is, the average image 61 (60) is a super-resolved image Ib having higher resolution in the X direction (that has undergone a super-resolution process in the X direction) than the first fluoroscopic X-ray image 10 and the second fluoroscopic X-ray image 20.

In this embodiment, the image processor 3b generates a super-resolved image Ic having higher resolution in the X and Y directions than the first fluoroscopic X-ray image 10, the second fluoroscopic X-ray image 20, the third fluoroscopic X-ray image 30, and the fourth fluoroscopic X-ray image 40 based on the first fluoroscopic X-ray image 10 (fluoroscopic X-ray image Ia), the second fluoroscopic X-ray image 20 (fluoroscopic X-ray image Ia), the third fluoroscopic X-ray image 30 (fluoroscopic X-ray image Ia), and the fourth fluoroscopic X-ray image 40 (fluoroscopic X-ray image Ia). Specifically, the image processor 3b generates the super-resolved image Ic by performing, in the Y direction, the same process as the division process in the X direction based on the divided images 50 (the divided image 51 and the divided image 52) that have undergone the division process in the X direction based on the first fluoroscopic X-ray image 10 and the second fluoroscopic X-ray image 20, and the divided images (a divided image 53 and a divided image 54) that have undergone the division process in the X direction based on the third fluoroscopic X-ray image 30 and the fourth fluoroscopic X-ray image 40. The divided image 53 and the divided image 54 are examples of a "first divided image" and a "second divided image" in the claims, respectively.

Figure 7:
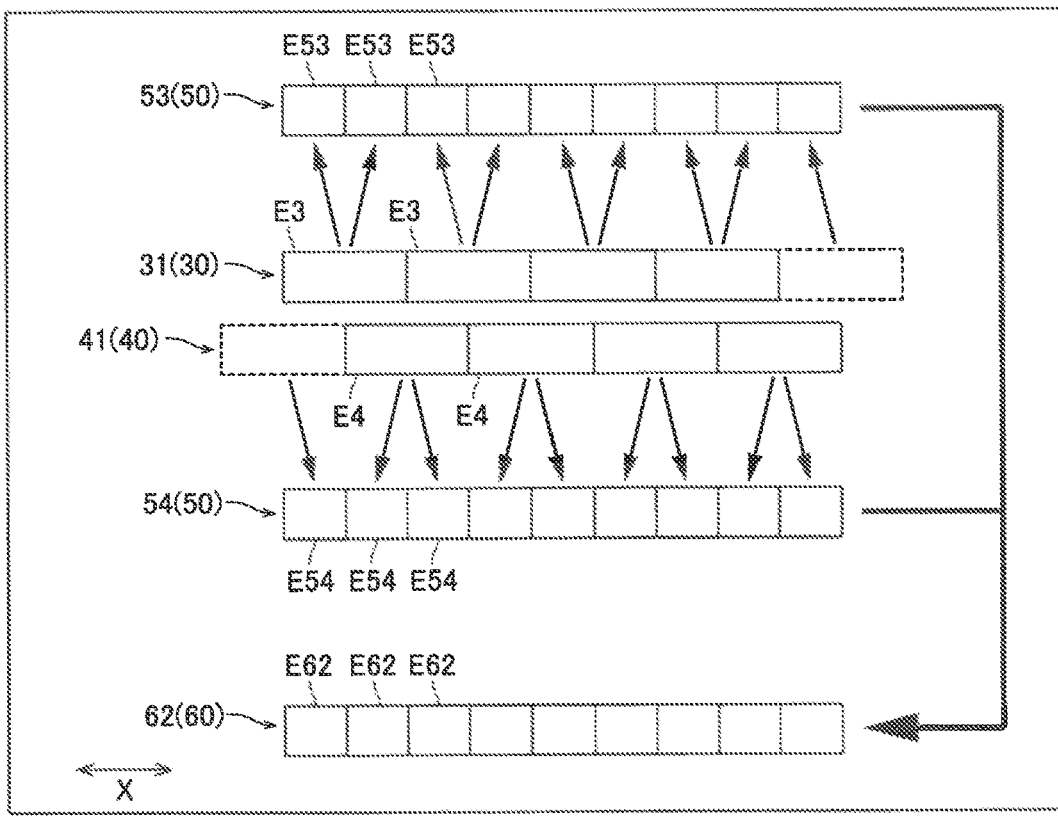
FIG. 7 is a diagram illustrating the super-resolution process in the X direction on a third fluoroscopic X-ray image and a fourth fluoroscopic X-ray image.

Specifically, as shown in FIG. 7, the image processor 3b generates the divided image 53 and the divided image 54 by performing the division process in the X direction based on the third fluoroscopic X-ray image 30 and the fourth fluoroscopic X-ray image 40, similarly to the divided image 51 and the divided image that have undergone the division process in the X direction based on the first fluoroscopic X-ray image 10 and the second fluoroscopic X-ray image 20. That is, the image processor 3b generates the divided image 53 by performing the division process in the X direction to divide the pixel values of pixels E3 in a third fluoroscopic X-ray image 31 (30) in the X direction, and generates the divided image 54 by performing the division process in the X direction to divide the pixel values of pixels E4 in a fourth fluoroscopic X-ray image 41 (40) in the X direction. The pixels E3 and E4 are examples of a "first pixel" and a "second pixel" in the claims, respectively.

The image processor 3b generates an average image 62 (60) obtained by averaging the pixel values of the pixels E in the divided image 53 and the divided image 54 corresponding to each other. That is, the image processor 3b averages the pixel value of a pixel E53 of the divided image 53 and the pixel value of a pixel E54 of the divided image 54 (corresponding to the pixel E53) to obtain a pixel E62 of the average image 62. Thus, as shown in FIG. 5, the average image 62 (60) having higher (doubled) resolution in the X direction than the third fluoroscopic X-ray image 30 and the fourth fluoroscopic X-ray image 40 is generated, similarly to the average image 61 (60). That is, the average image 62 (60) is a super-resolved image Ib having higher resolution in the X direction (that has undergone the super-resolution process in the X direction) than the third fluoroscopic X-ray image 30 and the fourth fluoroscopic X-ray image 40.

Figure 8:
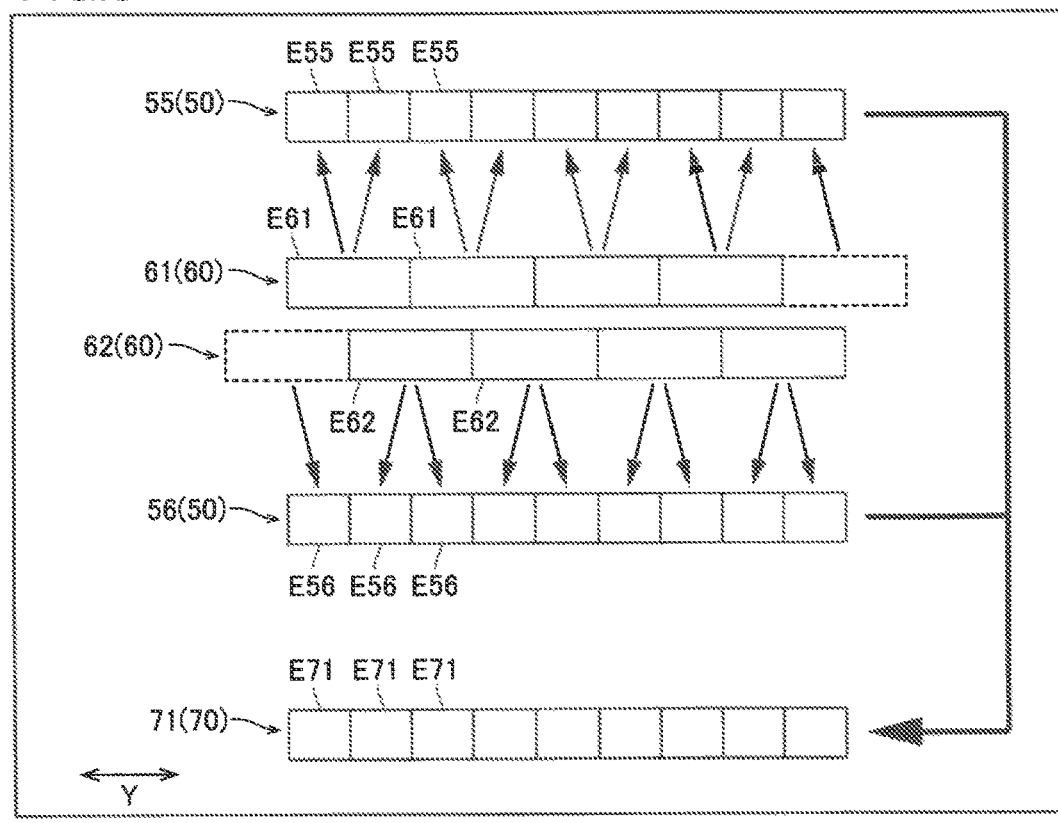
FIG. 8 is a diagram illustrating the super-resolution process in the Y direction based on two images that have undergone the super-resolution process in the X direction.

As shown in FIG. 8, the image processor 3b generates a divided image 55 and a divided image 56 by performing the division process in the Y direction based on the average image and the average image 62 (which are the super-resolved images Ib that have undergone the super-resolution process in the X direction). That is, the image processor 3b generates the divided image 55 by performing the division process in the Y direction to divide the pixel values of the pixels E61 in the average image 61 in the Y direction, and generates the divided image 56 by performing the division process in the Y direction to divide the pixel values of the pixels E62 in the average image 62 in the Y direction.

The image processor 3b generates an average image 71 (70) obtained by averaging the pixel values of the pixels E in the divided image 55 and the divided image 56 corresponding to each other. That is, the image processor 3b averages the pixel value of a pixel E55 of the divided image 55 and the pixel value of a pixel E56 of the divided image 56 (corresponding to the pixel E55) to obtain a pixel E71 of the average image 71. Thus, as shown in FIG. 5, the average image 71 (70) having higher (doubled) resolution in the Y direction than the average image 61 (60) and the average image 62 (60) is generated. Specifically, in the Y direction, the length L5 of one pixel Ec of the average image 71 (70) is half the length L4 of one pixel Eb of each of the average image 61 (60) and the average image 62 (60). That is, the average image 71 (70) is a super-resolved image Ic having higher resolution in the X and Y directions (that has undergone the super-resolution process in the X and Y directions) than the fluoroscopic X-ray images Ia (the first fluoroscopic X-ray image 10, the second fluoroscopic X-ray image 20, the third fluoroscopic X-ray image 30, and the fourth fluoroscopic X-ray image 40).

Figure 9:
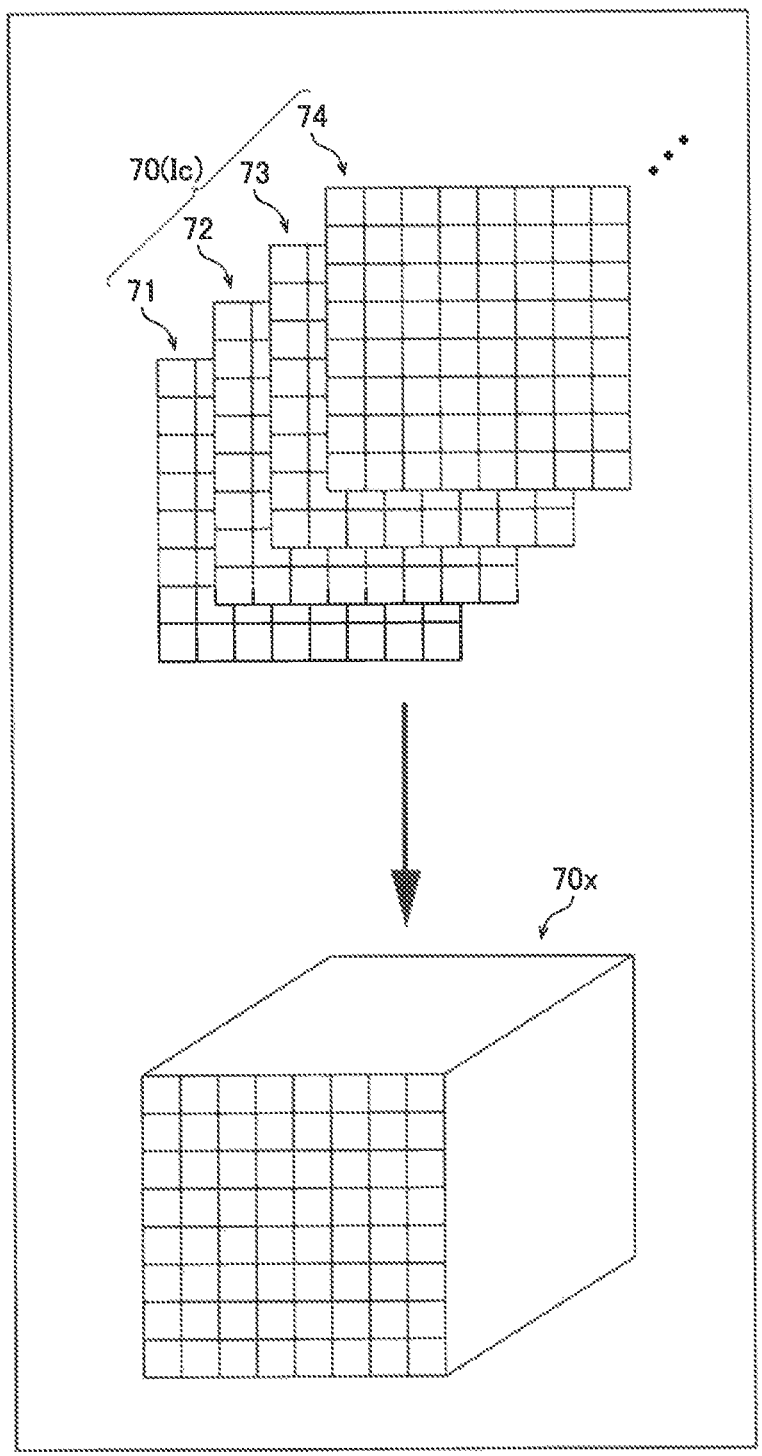
FIG. 9 is a diagram illustrating generation of a reconstructed image obtained by reconstructing a plurality of super-resolved images that have undergone the super-resolution process in the X and Y directions.

As shown in FIG. 9, the image processor 3b reconstructs the super-resolved image Ic (that has undergone the super-resolution process in the X and Y directions) to generate the reconstructed image 70x. That is, the image processor 3b generates the super-resolved image Ic with respect to a plurality of fluoroscopic X-ray images Ia acquired by tomographic imaging using the rotating stage 4. Specifically, the image processor 3b reconstructs the (two-dimensional) average images 71, 72, 73, 74, . . . , which are the super-resolved images Ic, to generate the three-dimensional reconstructed image 70x. The average image 72 is an average image 72 (70) that is a super-resolved image Ic generated from the first fluoroscopic X-ray image 12, the second fluoroscopic X-ray image 22, the third fluoroscopic X-ray image 32, and the fourth fluoroscopic X-ray image 42. The average image 73 is an average image 73 (70) that is a super-resolved image Ic generated from the first fluoroscopic X-ray image 13, the second fluoroscopic X-ray image 23, the third fluoroscopic X-ray image 33, and the fourth fluoroscopic X-ray image 43. The average image 74 is an average image 74 (70) that is a super-resolved image Ic generated from the first fluoroscopic X-ray image 14, the second fluoroscopic X-ray image 24, the third fluoroscopic X-ray image 34, and the fourth fluoroscopic X-ray image 44.

Super-Resolved Image Generation Flow

A flow of generating the super-resolved image Ic having higher resolution in the X and Y directions than the fluoroscopic X-ray image Ia is now described with reference to FIGS. 10 to 13. Prior to generation of the super-resolved image Ic, scan imaging is performed at the first position P1, the second position P2, the third position P3, and the fourth position P4 such that the first fluoroscopic X-ray image 10, the second fluoroscopic X-ray image 20, the third fluoroscopic X-ray image 30, and the fourth fluoroscopic X-ray image 40 are generated.

Figure 10:
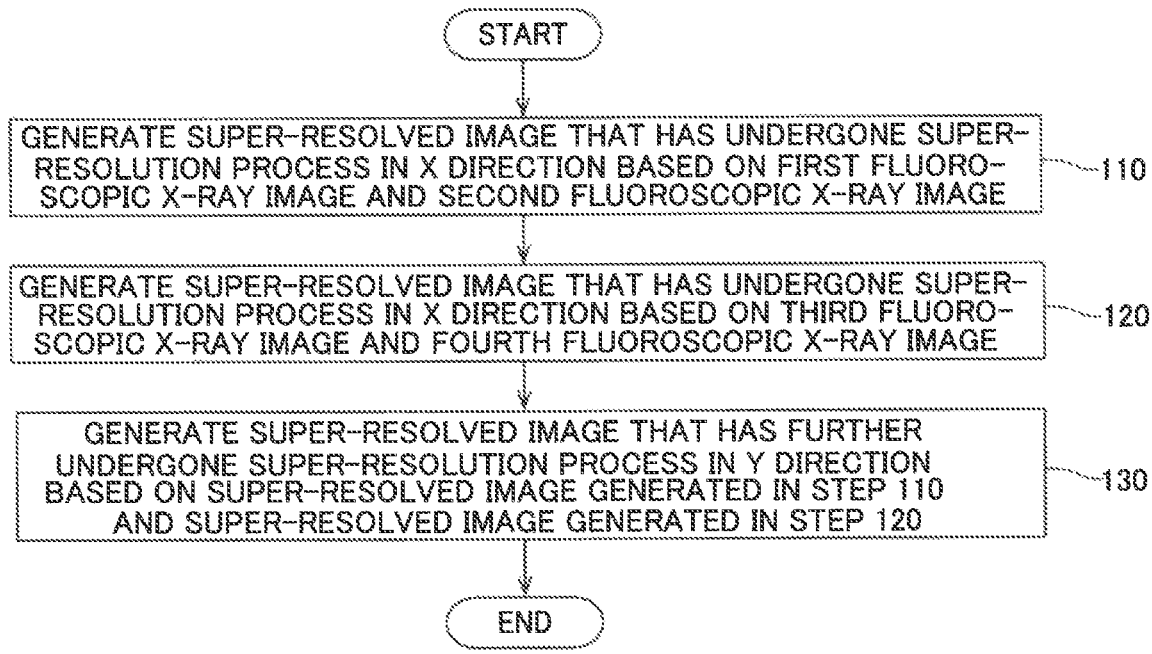
FIG. 10 is a super-resolved image generation flow.

First, as shown in FIG. 10, in step 110, the image processor 3b generates the super-resolved image Ib that has undergone the super-resolution process in the X direction based on the first fluoroscopic X-ray image 10 and the second fluoroscopic X-ray image 20.

Figure 11:
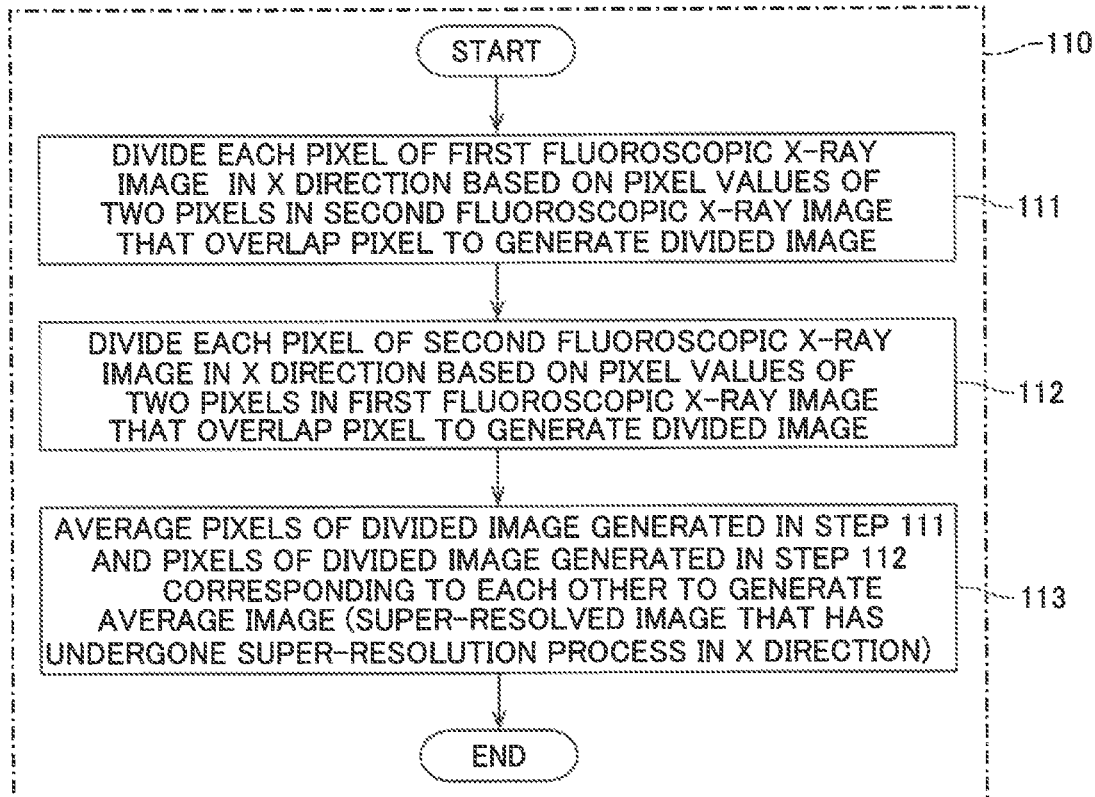
FIG. 11 is a flow of performing the super-resolution process in the X direction based on the first fluoroscopic X-ray image and the second fluoroscopic X-ray image.

Specifically, as shown in FIG. 11, in step 111, the image processor 3b generates the divided image 51 by dividing each pixel E1 of the first fluoroscopic X-ray image 10 in the X direction based on the pixel values of the two pixels E2 in the second fluoroscopic X-ray image 20 that overlap the pixel E1 when the first fluoroscopic X-ray image 10 and the second fluoroscopic X-ray image 20 are shifted in the X direction by the amount corresponding to the movement amount (of the X-ray detection position) and displayed in an overlapping manner.

Then, in step 112, the image processor 3b generates the divided image 52 by dividing each pixel E2 of the second fluoroscopic X-ray image 20 in the X direction based on the pixel values of the two pixels E1 in the first fluoroscopic X-ray image 10 that overlap the pixel E2 when the first fluoroscopic X-ray image 10 and the second fluoroscopic X-ray image 20 are shifted in the X direction by the amount corresponding to the movement amount (of the X-ray detection position) and displayed in an overlapping manner. The order of step 111 and step 112 may be reversed.

Then, in step 113, the image processor 3b averages the pixels E of the divided image 51 and the pixels E of the divided image 52 corresponding to each other to generate the average image 61 (the super-resolved image Ib that has undergone the super-resolution process in the X direction).

Then, as shown in FIG. 10, in step 120, the image processor 3b generates the super-resolved image Ib that has undergone the super-resolution process in the X direction based on the third fluoroscopic X-ray image 30 and the fourth fluoroscopic X-ray image 40. The order of step 110 and step 120 may be reversed.

Figure 12:
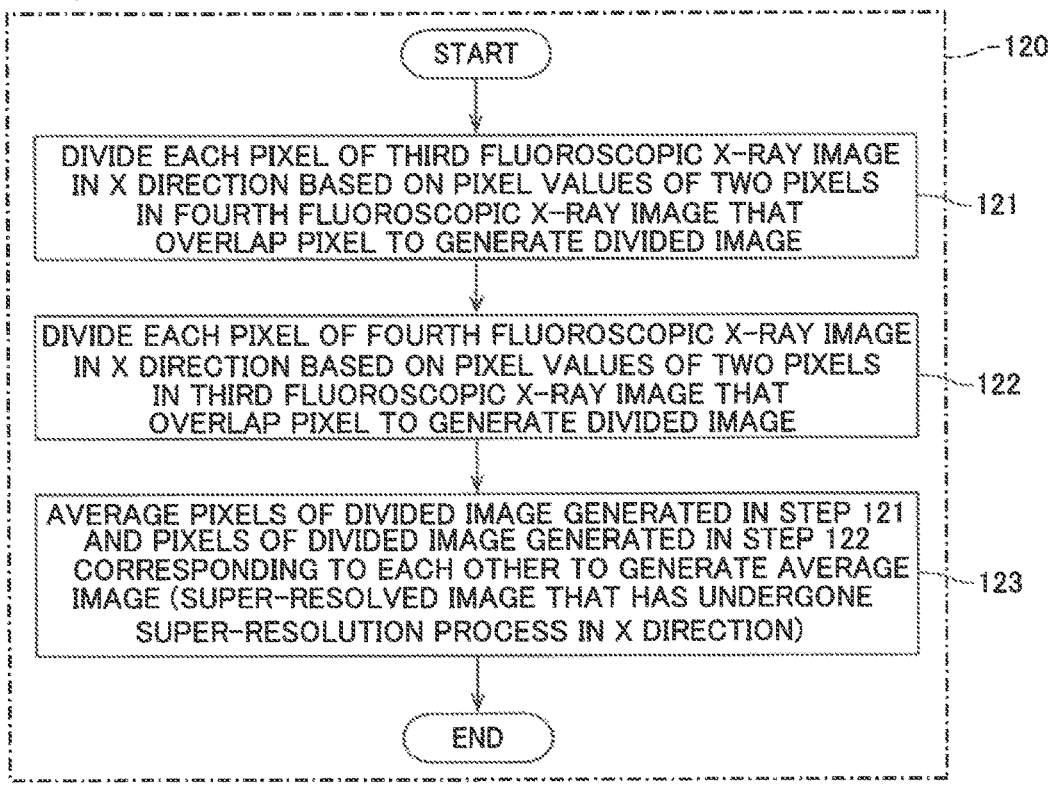
FIG. 12 is a flow of performing the super-resolution process in the X direction based on the third fluoroscopic X-ray image and the fourth fluoroscopic X-ray image.

Specifically, as shown in FIG. 12, in step 121, the image processor 3b generates the divided image 53 by dividing each pixel E3 of the third fluoroscopic X-ray image 30 in the X direction based on the pixel values of the two pixels E4 in the fourth fluoroscopic X-ray image 40 that overlap the pixel E3 when the third fluoroscopic X-ray image 30 and the fourth fluoroscopic X-ray image 40 are shifted in the X direction by the amount corresponding to the movement amount (of the X-ray detection position) and displayed in an overlapping manner.

Then, in step 122, the image processor 3b generates the divided image 54 by dividing each pixel E4 of the fourth fluoroscopic X-ray image 40 in the X direction based on the pixel values of the two pixels E3 in the third fluoroscopic X-ray image 30 that overlap the pixel E4 when the third fluoroscopic X-ray image 30 and the fourth fluoroscopic X-ray image 40 are shifted in the X direction by the amount corresponding to the movement amount (of the X-ray detection position) and displayed in an overlapping manner. The order of step 121 and step 122 may be reversed.

Then, in step 123, the image processor 3b averages the pixels E of the divided image 53 and the pixels E of the divided image 54 corresponding to each other to generate the average image 62 (the super-resolved image Ib that has undergone the super-resolution process in the X direction).

Then, as shown in FIG. 10, in step 130, the image processor 3b generates the super-resolved image Ic that has further undergone the super-resolution process in the Y direction based on the average image 61 and the average image (that are the super-resolved images Ib that have undergone the super-resolution process in the X direction).

Figure 13:
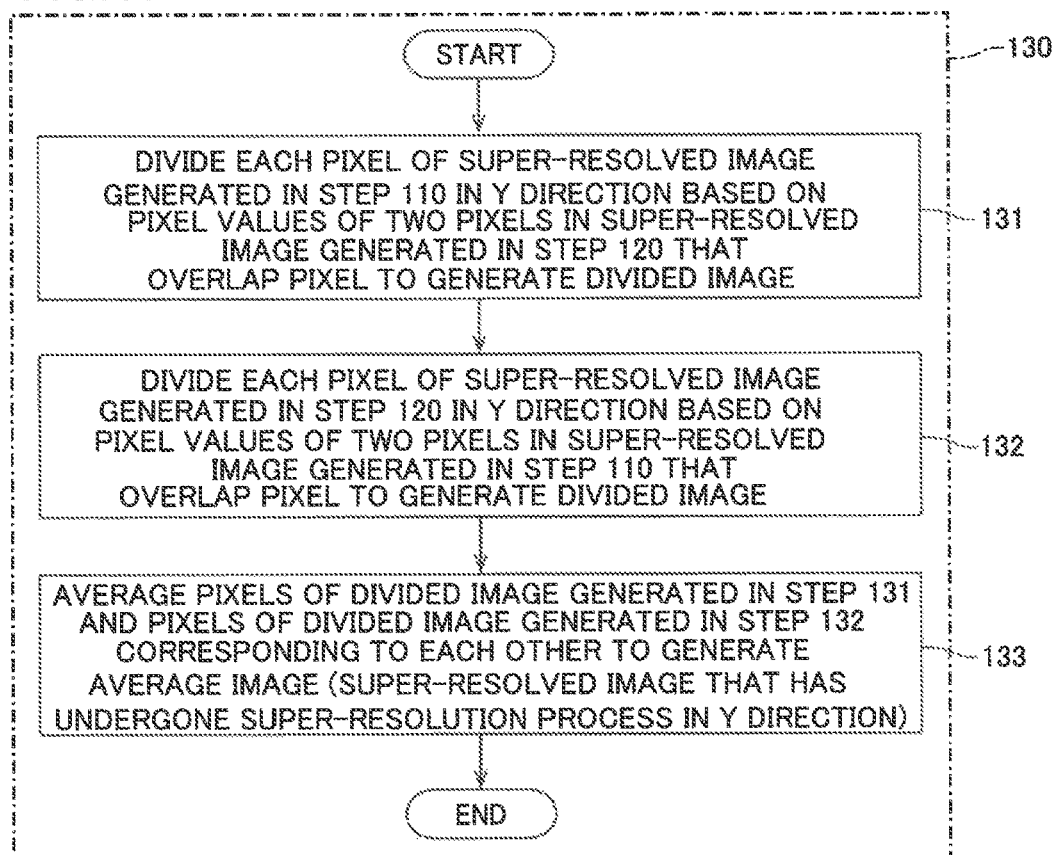
FIG. 13 is a flow of further performing the super-resolution process in the Y direction based on two images that have undergone the super-resolution process in the X direction.

Specifically, as shown in FIG. 13, in step 131, the image processor 3b generates the divided image 55 by dividing each pixel E61 of the average image 61 in the Y direction based on the pixel values of the two pixels E62 in the average image 62 that overlap the pixel E61 when the average image 61 and the average image 62 are shifted in the Y direction by the amount corresponding to the movement amount (of the X-ray detection position) and displayed in an overlapping manner.

Then, in step 132, the image processor 3b generates the divided image 56 by dividing each pixel E62 of the average image 62 in the Y direction based on the pixel values of the two pixels E61 in the average image 61 that overlap the pixel E62 when the average image 61 and the average image 62 are shifted in the Y direction by the amount corresponding to the movement amount (of the X-ray detection position) and displayed in an overlapping manner. The order of step 131 and step 132 may be reversed.

Then, in step 133, the image processor 3b averages the pixels E of the divided image 55 and the pixels E of the divided image 56 corresponding to each other to generate the average image 70 (the super-resolved image Ic that has undergone the super-resolution process in the X and Y directions).

Advantages of this Embodiment

In this embodiment, the following advantages are obtained.

In this embodiment, as described above, the image processor 3b is configured to generate the super-resolved image Ib having higher resolution in the X direction than the first fluoroscopic X-ray image 10 and the second fluoroscopic X-ray image 20 based on the divided image 50 (divided image 51) that has undergone the division process in the X direction to divide, in the X direction, the pixel value of each pixel E1 in the first fluoroscopic X-ray image 10 based on the pixel values of the two pixels E2 in the second fluoroscopic X-ray image 20 that overlap the pixel E1 when the first fluoroscopic X-ray image 10 and the second fluoroscopic X-ray image 20 are shifted in the X direction by the amount corresponding to the movement amount (of the X-ray detection position) and displayed in an overlapping manner. Accordingly, the pixel value of the pixel E1 can be divided in the X direction in consideration of the distribution of the actual pixel values by relatively simple calculation of dividing the pixel value based on the pixel values of the two pixels E2. That is, the calculation of simply dividing the pixel value based on the pixel values of the two pixels E2 is used, and thus it is not necessary to use sequential calculation performed in the conventional super-resolution process and a large number of parameters. Furthermore, the pixel E1 is divided in consideration of the distribution of the actual pixel values E2, and thus the super-resolved image Ib having higher resolution at least in the X direction than the first fluoroscopic X-ray image 10 and the second fluoroscopic X-ray image 20, in which a certain level of image quality is ensured, can be generated. Consequently, the super-resolved image Ib can be generated while an increase in the calculation time for generating the super-resolved image Ib is significantly reduced or prevented and a certain super-resolution effect (the effect of increasing the resolution without degrading the image quality) is ensured.

In this embodiment, as described above, the image processor 3b is configured to generate the super-resolved image Ib based on the divided image 50 (divided image 51) obtained by performing the division process on the pixel value of each pixel E1 of the first fluoroscopic X-ray image 10 based on the pixel values of the two pixels E2 in the second fluoroscopic X-ray image 20 that overlap the pixel E1 and the overlapping area ratio when the first fluoroscopic X-ray image 10 and the second fluoroscopic X-ray image 20 are shifted in the X direction by the amount corresponding to the movement amount (of the X-ray detection position) and displayed in an overlapping manner. Accordingly, in addition to the pixel values of the two pixels E2 that overlap the pixel E1, the overlapping area ratio of the two pixels E2 is taken into consideration, and thus the pixel E1 can be divided in the X direction while the distribution of the actual pixel values is more accurately considered. Consequently, as compared with a case in which the overlapping area ratio of the two pixels E2 is not taken into consideration, the super-resolved image Ib having higher resolution at least in the X direction than the first fluoroscopic X-ray image 10 and the second fluoroscopic X-ray image 20 and a better image quality can be generated.

In this embodiment, as described above, the image processor 3b is configured to generate the super-resolved image Ib based on the divided image 51 obtained by performing the division process on the pixel value of each pixel E1 in the first fluoroscopic X-ray image 10 based on the pixel values of the two pixels E2 in the second fluoroscopic X-ray image 20 that overlap the pixel E1 when the first fluoroscopic X-ray image 10 and the second fluoroscopic X-ray image 20 are shifted in the X direction by the amount corresponding to the movement amount (of the X-ray detection position) and displayed in an overlapping manner, and the divided image 52 obtained by performing the division process on the pixel value of each pixel E2 in the second fluoroscopic X-ray image 20 based on the pixel values of the two pixels E1 in the first fluoroscopic X-ray image 10 that overlap the pixel E2 when the first fluoroscopic X-ray image 10 and the second fluoroscopic X-ray image 20 are shifted in the X direction by the amount corresponding to the movement amount (of the X-ray detection position) and displayed in an overlapping manner. Accordingly, the super-resolved image Ib is generated in consideration of both the divided image 51 and the divided image 52, and thus the accuracy of dividing the pixel value in the X direction can be improved as compared with a case in which the super-resolved image Ib is generated in consideration of only one of the divided image 51 and the divided image 52. Consequently, as compared with a case in which the super-resolved image Ib is generated in consideration of only one of the divided image and the divided image 52, the super-resolved image Ib having higher resolution at least in the X direction than the first fluoroscopic X-ray image 10 and the second fluoroscopic X-ray image 20 and a better image quality can be generated.

In this embodiment, as described above, the image processor 3b is configured to generate the super-resolved image Ib by generating the average image 61 obtained by averaging the pixels E of the divided image 51 and the pixels E of the divided image 52 corresponding to each other. Accordingly, an error that occurs between the divided image 51 and the divided image 52 can be reduced as compared with a case in which the average image 61 is not generated, and thus the accuracy of dividing the pixel value in the X direction can be easily improved.

In this embodiment, as described above, the detector 2 is configured to detect X-rays at the third position P3 and the fourth position P4 translated from the first position P1 and the second position P2 in the Y direction orthogonal to the X direction by the movement amount smaller than the pixel size of the detector 2, respectively, in addition to the first position P1 and the second position P2. Furthermore, the image processor 3b is configured to generate the first fluoroscopic X-ray image 10, the second fluoroscopic X-ray image 20, the third fluoroscopic X-ray image 30, and the fourth fluoroscopic X-ray image 40 based on the X-rays detected at the first position P1, the second position P2, the third position P3, and the fourth position P4, respectively. Moreover, the image processor 3b is configured to generate the super-resolved image Ic having higher resolution in the X and Y directions than the first fluoroscopic X-ray image 10, the second fluoroscopic X-ray image 20, the third fluoroscopic X-ray image 30, and the fourth fluoroscopic X-ray image 40 by performing, in the Y direction, the same process as the division process in the X direction based on the divided image (51, 52) that has undergone the division process in the X direction based on the first fluoroscopic X-ray image 10 and the second fluoroscopic X-ray image 20, and the divided image (53, 54) that has undergone the division process in the X direction based on the third fluoroscopic X-ray image 30 and the fourth fluoroscopic X-ray image 40. Accordingly, the super-resolved image Ic having high resolution in the Y direction in addition to the X direction, in which a certain level of image quality is ensured, can be generated, and thus as compared with a case in which the resolution is high only in the X direction, the super-resolved image Ic in which the degree of resolution is not biased in the X direction and the Y direction can be generated. Furthermore, pixels E in a general display device have the same size in the row direction (X direction) and the column direction (Y direction) of detection elements 2a arranged in a matrix, and thus a post-process to display the super-resolved image Ic on a display device (not shown) such as an image interpolation process to adjust the pixel sizes in the X and Y directions can be simplified unlike a case in which the resolution is different in the X and Y directions.

In this embodiment, as described above, the image processor 3b is configured to virtually generate, based on the pixel value of one overlapping pixel E2, another overlapping pixel E2 when there is only one pixel E2 that overlaps the pixel E1 of the first fluoroscopic X-ray image 10 at the end of the second fluoroscopic X-ray image 20 when the first fluoroscopic X-ray image 10 and the second fluoroscopic X-ray image 20 are shifted in the X direction by the amount corresponding to the movement amount (of the X-ray detection position) and displayed in an overlapping manner. Accordingly, another overlapping pixel E is virtually generated such that even when there is only one pixel E2 that overlaps the pixel E1 located at the end of the first fluoroscopic X-ray image 10, calculation of dividing the pixel E1 can be reliably performed. Furthermore, the image processor 3b is configured to virtually generate, based on the pixel value of one overlapping pixel E1, another overlapping pixel E1 when there is only one pixel E1 that overlaps the pixel E2 of the second fluoroscopic X-ray image 20 at the end of the first fluoroscopic X-ray image 10. Accordingly, another overlapping pixel E1 is virtually generated such that even when there is only one pixel E1 that overlaps the pixel E2 located at the end of the second fluoroscopic X-ray image 20, calculation of dividing the pixel E2 can be reliably performed.

In this embodiment, as described above, the detector 2 is configured to detect X-rays radiated from the X-ray source 1 at the first position P1 (third position P3) and the second position P2 (fourth position P4), which is translated in the X direction by the distance equal to the length L5 half the pixel Ea size (length L4) of the detector 2 from the first position P1 (third position P3). Accordingly, the overlapping area ratio of the two pixels E2 (pixels E4) is equal (1:1), and thus the pixel value of the pixel E1 (pixel E3) can be divided in the X direction using the ratio of the pixel values themselves of the two pixels E2 (pixels E4) that overlap the pixel E1 (pixel E3). Consequently, calculation in the division process can be simplified as compared with a case in which division is performed using the overlapping area ratio of the two pixels E2 (pixels E4) other than ½, and thus an increase in the calculation time for generating the super-resolved image Ib can be further significantly reduced or prevented.

In this embodiment, as described above, the detector 2 is configured to perform tomographic imaging by alternately repeating the detection operation to detect X-rays radiated from the X-ray source 1 from a plurality of directions while rotating with the X direction as the rotation axis and translation in the X direction. Accordingly, in the X-ray imaging apparatus 100 that performs non-helical scan-type tomographic imaging, the super-resolved images Ib and Ic can be generated while an increase in the calculation time for generating the super-resolved image Ib is significantly reduced or prevented and a certain super-resolution effect is ensured.

MODIFIED EXAMPLES

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the example in which the image processor 3b generates the virtual pixel E such that the virtual pixel E has a pixel value equal to the pixel value of the adjacent pixel E has been shown in the aforementioned embodiment, the present invention is not limited to this. In the present invention, the image processor may be configured to generate the virtual pixel such that the virtual pixel has a pixel value different from that of the adjacent pixel.

While the example in which the X-ray detection position is translated by a distance equal to the length L5, which is half the length L4 of one pixel Ea, and the image processor 3b divides, in half, the pixel value of each pixel E1 (pixel E3) of the first fluoroscopic X-ray image 10 (third fluoroscopic X-ray image 30) based on the pixel values of the two pixels E2 (pixels E4) in the second fluoroscopic X-ray image 20 (fourth fluoroscopic X-ray image 40) that overlap the pixel E1 (pixel E3) in half when the first fluoroscopic X-ray image 10 (third fluoroscopic X-ray image 30) and the second fluoroscopic X-ray image 20 (fourth fluoroscopic X-ray image 40) are shifted in the X direction by the amount corresponding to the movement amount (of the X-ray detection position) in an overlapping manner has been shown in the aforementioned embodiment, the present invention is not limited to this. In the present invention, the X-ray detection position may be translated by a distance longer than half the length of one pixel or may be translated by a distance shorter than half the length of one pixel. In this case, the image processor may generate the divided image by performing the division process on the pixel value of each "first pixel (in the claims)" of the "first image (in the claims)" based on the pixel values of the two "second pixels (in the claims)" in the "second image (in the claims)" that overlap the "first pixel" and the overlapping area ratio.

While the example in which the image processor 3b generates the divided image 50 by dividing the fluoroscopic X-ray images Ia based on X-rays detected at positions translated in either the X direction or the Y direction has been shown in the aforementioned embodiment, the present invention is not limited to this. In the present invention, the image processor may generate the divided image by dividing the fluoroscopic X-ray images based on X-rays detected at positions translated in both the X and Y directions (translated diagonally with respect to the X and Y directions).

While the example in which the image processor 3b generates the super-resolved image Ib by generating the average image 60 obtained by averaging the pixels E of the two divided images 50 corresponding to each other has been shown in the aforementioned embodiment, the present invention is not limited to this. In the present invention, the image processor may process one divided image itself as a super-resolved image.

While the example in which the X-ray imaging apparatus 100 generates the first fluoroscopic X-ray image 10, the second fluoroscopic X-ray image 20, the third fluoroscopic X-ray image 30, and the fourth fluoroscopic X-ray image 40 by performing scan imaging at the first position P1, the second position P2, the third position P3, and the fourth position P4 prior to generation of the super-resolved image Ic has been shown in the aforementioned embodiment, the present invention is not limited to this. In the present invention, when the fluoroscopic X-ray image required to generate one super-resolved image is generated, generation of one super-resolved image may be started before the fluoroscopic X-ray image required to generate another super-resolved image is generated. For example, as applied to the example of the above embodiment, when the first fluoroscopic X-ray image 10 and the second fluoroscopic X-ray image 20 are generated, generation of the super-resolved image Ib that has undergone the super-resolution process in the X direction may be started based on the first fluoroscopic X-ray image 10 and the second fluoroscopic X-ray image 20 even when the third fluoroscopic X-ray image 30 and the fourth fluoroscopic X-ray image 40 are not generated.

While the example in which the image processor 3b generates the super-resolved image Ib based on the two fluoroscopic X-ray images Ia has been shown in the aforementioned embodiment, the present invention is not limited to this. In the present invention, the image processor may generate the super-resolved image based on three or more fluoroscopic X-ray images.

While the example in which the image processor 3b generates the reconstructed image 70x by reconstructing the super-resolved image Ic that has undergone the super-resolution process in the X and Y directions has been shown in the aforementioned embodiment, the present invention is not limited to this. In the present invention, the image processor may generate the reconstructed image by reconstructing the super-resolved image that has undergone the super-resolution process in only one of the X direction and the Y direction. In this case, a fluoroscopic X-ray image having a different X-ray detection position in a direction in which the super-resolution process is not performed becomes unnecessary.

While the example in which the super-resolved images Ib and Ic are generated in the X-ray imaging apparatus 100 that performs non-helical scan-type tomographic imaging has been shown in the aforementioned embodiment, the present invention is not limited to this. In the present invention, the super-resolved images may be generated in an X-ray imaging apparatus that performs helical scan-type tomographic imaging (that operates helically). Alternatively, the super-resolved images may be generated in an X-ray imaging apparatus that does not perform tomographic imaging.

DESCRIPTION OF REFERENCE NUMERALS

1: X-ray source
2: detector
3b: image processor
5: detector moving mechanism (moving mechanism)
10 (11, 12, 13, 14): first fluoroscopic X-ray image (first image)
20 (21, 22, 23, 24): second fluoroscopic X-ray image (second image)
30 (31, 32, 33, 34): third fluoroscopic X-ray image (third image)
40 (41, 42, 43, 44): fourth fluoroscopic X-ray image (fourth image)
50: divided image
51, 53: divided image (first divided image)
52, 54: divided image (second divided image)
60 (61, 62): average image
90: rotation axis
100: X-ray imaging apparatus
E (Ea, Eb, Ec): pixel
E1, E3: pixel (first pixel)
E2, E4: pixel (second pixel)
Ib, Ic: super-resolved image
P1: first position
P2: second position
P3: third position
P4: fourth position

The invention claimed is:

1. An X-ray imaging apparatus comprising:
an X-ray source;
a detector configured to detect X-rays radiated from the X-ray source at a first position and a second position translated in a first direction by a movement amount smaller than a pixel size of the detector from the first position;
an image processor configured to generate a first image based on the X-rays detected at the first position, the image processor being configured to generate a second image based on the X-rays detected at the second position; and
a moving mechanism configured to move an X-ray detection position of the detector between the first position and the second position; wherein
the image processor is configured to generate a super-resolved image having higher resolution in the first direction than the first image and the second image based on a divided image that has undergone a division process in the first direction to divide, in the first direction, a pixel value of a first pixel in one of the first image and the second image based on pixel values of two pixels in the other of the first image and the second image that overlap the first pixel when the first image and the second image are shifted in the first direction by an amount corresponding to the movement amount and displayed in an overlapping manner.

2. The X-ray imaging apparatus according to claim 1, wherein the image processor is configured to generate the super-resolved image based on the divided image obtained by performing the division process on the pixel value of the first pixel in one of the first image and the second image based on the pixel values of the two pixels in the other of the first image and the second image that overlap the first pixel and an overlapping area ratio when the first image and the second image are shifted in the first direction by the amount corresponding to the movement amount and displayed in the overlapping manner.

3. The X-ray imaging apparatus according to claim 2, wherein the detector is configured to detect the X-rays radiated from the X-ray source at the first position and the second position translated in the first direction by a distance equal to a length half the pixel size of the detector from the first position.

4. The X-ray imaging apparatus according to claim 1, wherein the image processor is configured to generate the super-resolved image based on a first divided image obtained by performing the division process on the pixel value of the first pixel in the first image based on the pixel values of the two pixels in the second image that overlap the first pixel when the first image and the second image are shifted in the first direction by the amount corresponding to the movement amount and displayed in the overlapping manner, and a second divided image obtained by performing the division process on a pixel value of a second pixel in the second image based on pixel values of two pixels in the first image that overlap the second pixel when the first image and the second image are shifted in the first direction by the amount corresponding to the movement amount and displayed in the overlapping manner.

5. The X-ray imaging apparatus according to claim 4, wherein the image processor is configured to generate the super-resolved image by generating an average image obtained by averaging a pixel of the first divided image and a pixel of the second divided image corresponding to each other.

6. The X-ray imaging apparatus according to claim 1, wherein
the detector is configured to detect X-rays at a third position and a fourth position respectively translated in a second direction orthogonal to the first direction by the movement amount smaller than the pixel size of the detector from the first position and the second position, in addition to the first position and the second position; and
the image processor is configured to:
generate the first image, the second image, a third image, and a fourth image based on the X-rays detected at the first position, the second position, the third position, and the fourth position, respectively; and
generate the super-resolved image having higher resolution in the first and second directions than the first image, the second image, the third image, and the fourth image by performing, in the second direction, a same process as the division process in the first direction based on the divided image that has undergone the division process in the first direction based on the first image and the second image, and the divided image that has undergone the division process in the first direction based on the third image and the fourth image.

7. The X-ray imaging apparatus according to claim 1, wherein the image processor is configured to virtually generate, based on a pixel value of one overlapping pixel, another overlapping pixel when there is only one pixel that overlaps the first pixel of one of the first image and the second image at an end of the other of the first image and the second image when the first image and the second image are shifted in the first direction by the amount corresponding to the movement amount and displayed in the overlapping manner.

8. The X-ray imaging apparatus according to claim 1, wherein the detector is configured to perform tomographic imaging by alternately repeating detection operation to detect the X-rays radiated from the X-ray source from a plurality of directions while rotating with a third direction as a rotation axis and translation in the third direction.

* * * * *